US009943659B2

(12) United States Patent
Chodkowski (10) Patent No.: US 9,943,659 B2
(45) Date of Patent: Apr. 17, 2018

(54) LEVER ADJUSTMENT ASSEMBLY FOR MASK

(71) Applicant: KONINKLIJKE PHILIPS N.V., Eindhoven (NL)

(72) Inventor: Lauren Patricia Chodkowski, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 721 days.

(21) Appl. No.: 14/380,842

(22) PCT Filed: Feb. 1, 2013

(86) PCT No.: PCT/IB2013/050867
§ 371 (c)(1),
(2) Date: Aug. 25, 2014

(87) PCT Pub. No.: WO2013/128309
PCT Pub. Date: Sep. 6, 2013

(65) Prior Publication Data
US 2015/0007824 A1  Jan. 8, 2015

Related U.S. Application Data

(60) Provisional application No. 61/605,242, filed on Mar. 1, 2012.

(51) Int. Cl.
*A61M 16/06* (2006.01)
(52) U.S. Cl.
CPC .......... *A61M 16/065* (2014.02); *A61M 16/06* (2013.01); *A61M 16/0605* (2014.02);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 3,422,532 A * 1/1969 Ballard ................ A01G 3/0475
30/252
4,899,420 A * 2/1990 Bye .......................... E05D 7/121
16/16
(Continued)

FOREIGN PATENT DOCUMENTS

DE      3927038 A1    2/1991
DE      3927038 C2    8/1993
(Continued)

*Primary Examiner* — (Jackie) Tan-Uyen T Ho
*Assistant Examiner* — Joseph D Boecker
(74) *Attorney, Agent, or Firm* — Michael W. Haas (57) ABSTRACT

A respiratory interface device is provided that includes a mask (10) and a brace (40) assembly. The mask has a faceplate (12) and a cushion (15), and the brace assembly has a brace body (42) and a lever assembly (44). The brace body is coupled to the mask faceplate, and the lever assembly has at least one lever arm (70) and at least one actuator assembly (72) for each lever arm. The at least one lever arm has a body (76) and a pivot assembly (90). The lever arm body is pivotally coupled to the brace body at the pivot assembly. The lever arm body is structured to move between two positions, a first position, where the lever arm body does not effectively engage a portion of the mask, and a second position, wherein the lever arm body effectively engages a portion of the mask.

11 Claims, 8 Drawing Sheets

(52) U.S. Cl.
CPC .... *A61M 16/0622* (2014.02); *A61M 16/0655* (2014.02); *A61M 16/0683* (2013.01); *A61M 16/0611* (2014.02); *A61M 16/0616* (2014.02); *A61M 16/0633* (2014.02)

(58) Field of Classification Search
CPC .......... A61M 16/0633; A61M 16/0638; A61M 16/0644; A61M 16/065; A61M 16/0683; A62B 7/00; A62B 7/14; A62B 9/04; A62B 18/00; A62B 18/02; A62B 18/025; A62B 18/04; A62B 18/084
USPC ........................................ 128/206.21, 206.24
See application file for complete search history.

(56) References Cited

U.S. PATENT DOCUMENTS

| | | | |
|---|---|---|---|
| 5,346,447 A * | 9/1994 | Stearns | A63B 23/0211 482/142 |
| 6,497,232 B2 * | 12/2002 | Fecteau | A62B 18/084 128/201.24 |
| 2003/0209241 A1 | 11/2003 | Fournier | |
| 2004/0045551 A1 * | 3/2004 | Eaton | A61M 16/06 128/206.21 |
| 2004/0099272 A1 * | 5/2004 | Kwok | A61M 16/06 128/206.21 |
| 2005/0072428 A1 * | 4/2005 | Ho | A61M 16/06 128/205.25 |
| 2007/0044804 A1 | 3/2007 | Matula, Jr. | |
| 2007/0062537 A1 | 3/2007 | Chiesa | |
| 2010/0000539 A1 | 1/2010 | Woodard | |
| 2011/0232647 A1 | 9/2011 | Ho | |

FOREIGN PATENT DOCUMENTS

| | | |
|---|---|---|
| DE | 102009051781 A1 | 5/2011 |
| EP | 0401307 B2 | 1/2002 |

* cited by examiner

LEVER ADJUSTMENT ASSEMBLY FOR MASK

CROSS-REFERENCE TO RELATED APPLICATIONS

This patent application claims the priority benefit under 35 U.S.C. § 371 of international patent application no. PCT/IB2013/050867, filed Feb. 1, 2013, which claims the priority benefit under 35 U.S.C. § 119(e) of U.S. Provisional Application No. 61/605,242 filed on Mar. 1, 2012, the contents of which are herein incorporated by reference.

BACKGROUND OF THE INVENTION

1. Field of the Invention

The present invention pertains to respiratory interface devices for communicating a flow of gas with an airway of a user, and, in particular, to a respiratory interface device that includes a mask and a lever, where actuation of the lever moves a portion of the mask toward the patient.

2. Description of the Related Art

A variety of respiratory masks are known which cover the areas surrounding the nose and/or mouth of a human user and that are designed to create an effective fit against the user's face. Typically, gases can be provided at a positive pressure within the mask for consumption by the user. The uses for such masks include high altitude breathing (aviation applications), swimming, mining, fire fighting, and various medical diagnostic and therapeutic applications.

One requisite of many of these masks, particularly medical respiratory masks, is that they provide an effective fit against the user's face and that the mask contours with the user's face to limit or prevent leakage of the gas being supplied. A common type of mask incorporates a single-piece faceplate or a two-piece faceplate, having an upper portion (e.g., to cover the nasal portion of a human user's face) and lower portion (e.g., to cover the mouth portion of a human user's face) that are unitary or coupled together by a flexible member. See, for example, U.S. Patent Pub. 2011/0232647 the contents of which are incorporated herein by reference.

The respiratory masks that are known also have a sealing surface or cushion around the periphery of the mask to seal against the user's face. The cushion is typically attached to the faceplate. Such masks have performed well when the fit is good between the contours of the seal surface and the corresponding contours of the user's face. This may occur, for example, if the mask provides a good fit against the user's face and the mask contours with the user's face. If the fit is not good, there will be gaps in the mask-to-face interface resulting in gas leaking from the mask at the gaps. Considerable force will be required to compress the mask member to close the gaps and attain a satisfactory seal in those areas where the gaps occur.

Typically, this required force will be provided by straps that are connected to the mask to securely fit the mask to the face of the user. Such force is undesirable because it produces high pressure points elsewhere on the face of the user where the mask contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow.

One area of the cushion that is prone to being spaced from the user's face is the area about the bridge of the nose. That is, it is not uncommon to have a gap between the cushion and the user's face at the bridge of the nose or adjacent the bridge of the nose. When such a gap occurs, the user may adjust the straps by tightening or loosening the straps, as discussed above, or by moving the position of the straps relative to the user's face. Typically, the user would move the straps to a higher position on their face. This adjustment, however, places the straps closer to the user's eyes, which is generally considered to be uncomfortable. Alternatively, the respiratory interface device may be provided with additional straps so as to allow for better positioning of the respiratory interface device relative to the user's face. Additional straps, however, are also generally considered to be uncomfortable.

SUMMARY OF THE INVENTION

One embodiment of the present invention provides a respiratory interface device including a mask and a brace assembly. The mask has a faceplate and a patient contacting cushion. The patient contacting cushion is coupled to, and extends about, the faceplate. The brace assembly has a brace body and a lever assembly. The brace body has a central portion, the central portion having an outer side and an inner side. The brace body central portion is structured to be, and is, coupled to the mask faceplate. The lever assembly has at least one lever arm and at least one actuator assembly for each lever arm. The at least one lever arm has a body with a first end, a second end and a medial portion therebetween. The lever arm body further includes a pivot assembly disposed on the lever arm body medial portion. The lever arm body is pivotally coupled to the brace body at the pivot assembly. The lever arm body is structured to move between two positions, a first position, wherein the lever arm body does not effectively engage a portion of the mask (i.e., does not move the mask), and a second position, wherein the lever arm body effectively engages a portion of the mask.

It is a further object of this invention to provide a method of using a respiratory interface device, the respiratory interface device including a mask and a brace assembly. The mask has a faceplate and a patient contacting cushion. The patient contacting cushion is coupled to, and extends about, the faceplate. The brace assembly has a brace body and a lever assembly. The brace body has a central portion, the central portion having an outer side and an inner side. The brace body central portion is structured to be, and is, coupled to the mask faceplate. The lever assembly has at least one lever arm and at least one actuator assembly for each lever arm. The at least one lever arm has a body with a first end, a second end and a medial portion therebetween. The lever arm body further includes a pivot assembly disposed on the lever arm body medial portion. The lever arm body is pivotally coupled to the brace body at the pivot assembly. The lever arm body is structured to move between two positions, a first position, wherein the lever arm body does not effectively engage a portion of the mask, and a second position, wherein the lever arm body effectively engages a portion of the mask. The method includes the steps of positioning the mask over the patient's nose and mouth thereby creating a generally continuous seal between the patient's face and the cushion, and, adjusting the at least one lever arm body so as to create a more complete seal between the patient's face and the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, a "contact coupling" means that contacting parts are biased toward each other. That is, parts that merely contact each other without any bias do not form a "contact coupling."

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall means that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. Further, as used herein, "inwardly" means in a direction toward the user's face and "outwardly" means in a direction away from the user's face.

As used herein, when discussing an element moving between two positions, e.g. a rod moving between a first position and a second position, "between" means at the first or at the second position, as well as any position therebetween.

As used herein, a "coupling" is one element of a coupling assembly. That is, a coupling assembly includes at least two elements, or couplings, that are structured to be coupled together. It is understood that the elements of a coupling assembly correspond to each other. For example, in a coupling assembly, if one coupling element is a bolt, the other coupling element is a nut. As a further example, in a coupling assembly, if one coupling element is a snap socket, the other coupling element is a snap plug. Further, it is understood that the two elements of a coupling assembly may not be described at the same time. It is further understood that coupling elements will be described by their location and that the other coupling element of the coupling assembly will have a similar description. For example, a mask may have a "first cheek coupling" and a brace may have a "first cheek coupling." Thus, it is understood that when the brace and the mask are coupled, the "mask first cheek coupling" and the "brace first cheek coupling" are elements of a coupling assembly that correspond to each other as described above.

As used herein, the "bridge" of the nose is the area of the nose between the eyes. As used herein, the "dorsum" of the nose is the elongated area of the nose below the bridge and above the tip. The "dorsum" is, typically, aligned with the centerline of the face. The sides of the nose are not part of the dorsum. As used herein, "aligned" means "on the same line as" or "parallel to."

As used herein, "effectively engage," when used in conjunction with a lever arm contacting a mask, means that the lever arm contacts, biases, and deforms the mask. The degree of deformation caused by an "effective engagement" may be very slight. A lever arm that contacts a mask without applying bias and without deforming the mask does not "effectively engage" the mask. As used herein, "a portion of" means less than the whole. Thus, a lever arm that effectively engages "a portion of" a mask does not bias the entire mask.

As used herein, a "semi-flexible member" is a malleable member that maintains its shape when exposed to no force or slight forces, but may be deformed when exposed to stronger forces. For example, a wire or twist tie are commonly known "semi-flexible members" that maintain their shape when exposed to a force, such as, but not limited to, their own weight or a slight breeze, but may easily be bent by a human. As used herein, "a generally continuous seal" may have a gap or may gap when the user moves. As used herein, "a more complete seal" has a gap that is shorter in length than a gap of a generally continuous seal, or, is resistant to gapping when the user moves.

Figure 1:
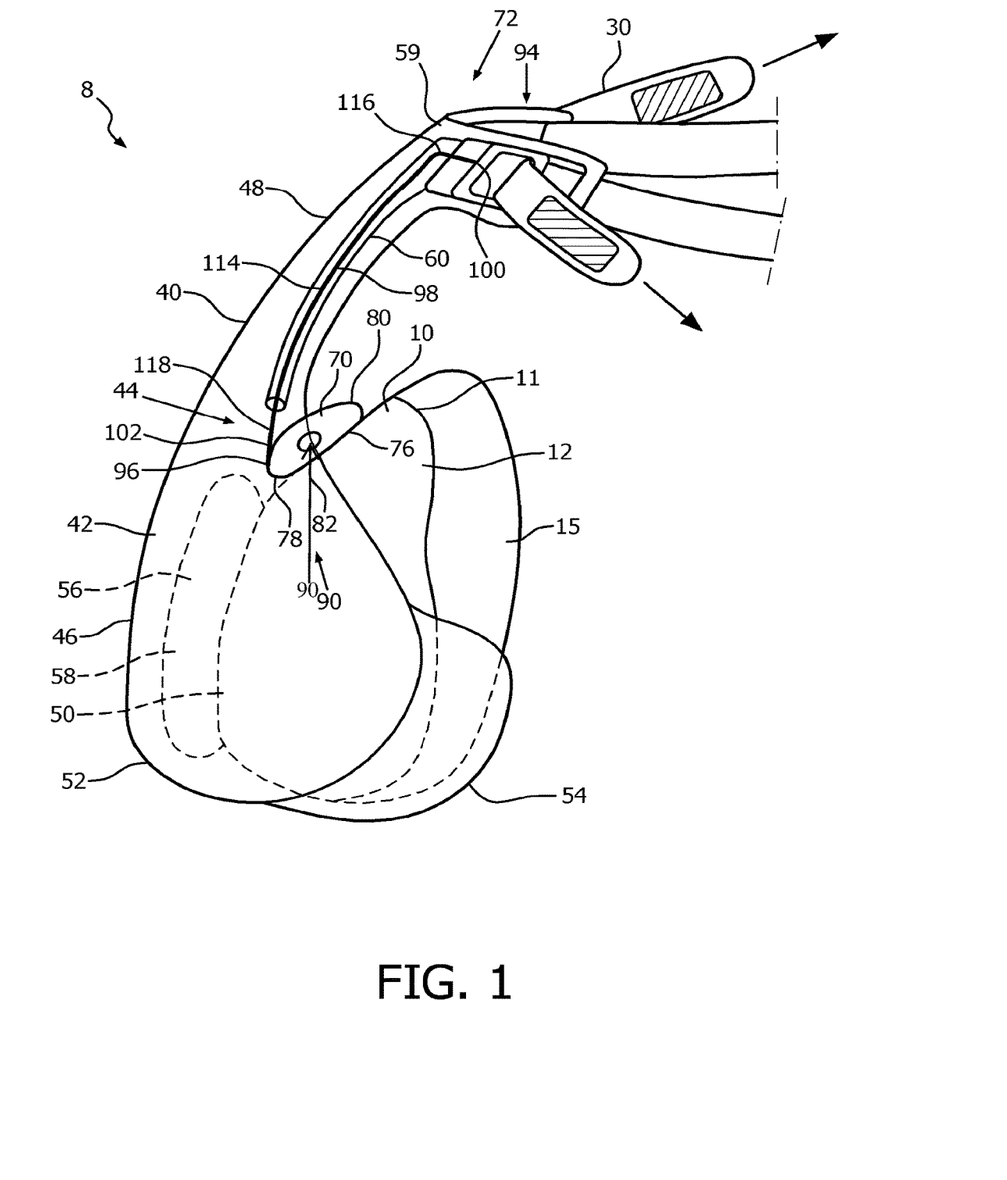
FIG. 1 is a side isometric view of a respiratory interface device according to an embodiment of the invention.

FIG. 1 is a side view of a respiratory interface device 8 according to an exemplary embodiment of the invention. Respiratory interface device 8 includes a respiratory mask 10 and a brace assembly 40. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV™) device, proportional positive airway pressure (PPAP) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory mask 10 includes a body 11 with a faceplate 12 and a cushion 15, discussed below. In an exemplary embodiment, faceplate 12 is substantially rigid. In an exemplary embodiment, shown in FIG. 1, faceplate 12 is a single piece structured to cover the user's nose and mouth. In this embodiment, body 11 is coextensive with faceplate 12. In another exemplary embodiment, shown in FIG. 2, faceplate 12 has upper portion 14 and lower portion 16. In this embodiment, body 11 further includes a substantially flexible connecting member 18 that extends between upper and lower portions 14 and 16, respectively. Connecting member 18 is structured to at least partially connect upper portion 14 to lower portion 16. Specifically, a first side of connecting member 18 is coupled to upper portion 14 and a second, opposite side, is coupled to lower portion 16. Upper and lower portions 14, 16 are typically, although not necessarily, generally rigid. That is, faceplate upper portion 14 may also be identified as a "first substantially rigid portion" and faceplate lower portion 16 may be identified as a "second substantially rigid portion."

Figure 2:
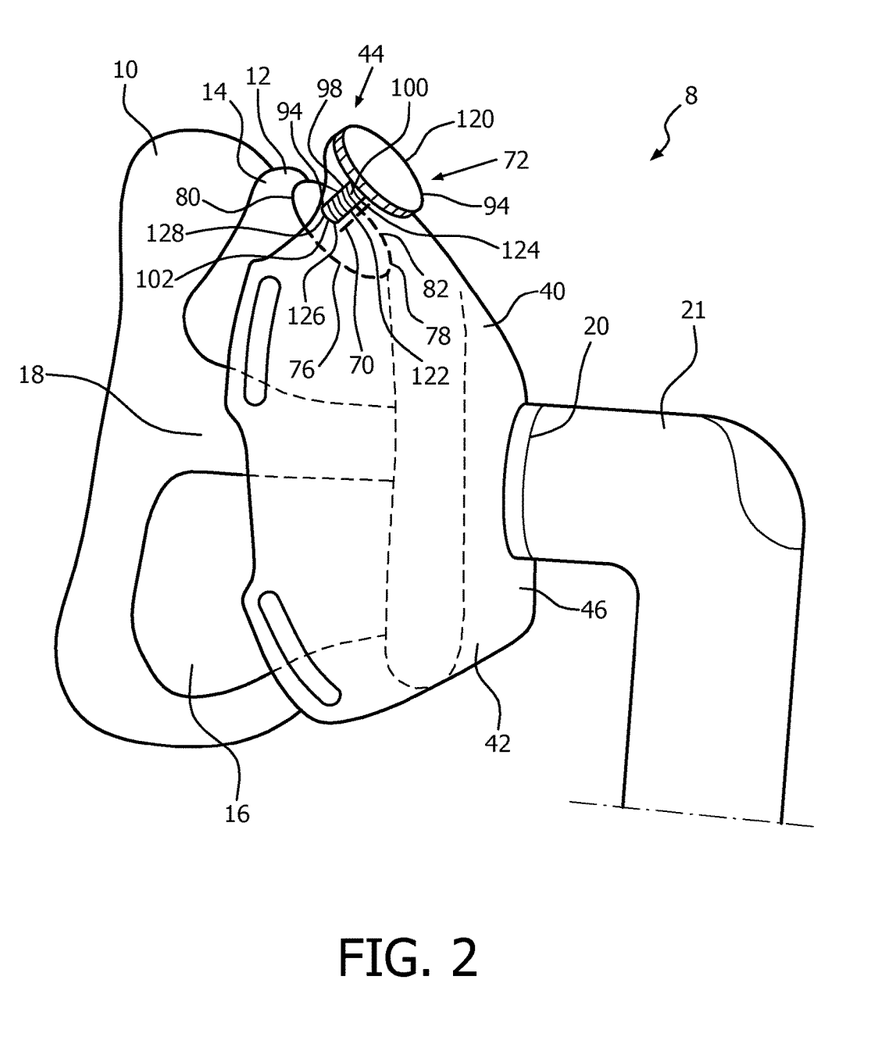
FIG. 2 is a side isometric view of a respiratory interface device according to another embodiment of the invention.

Connecting member 18 is a flexible, resilient member. In an exemplary embodiment of the present invention, connecting member 18 is made of, for example, a thermoplastic or thermoelastic material, including but not limited to an elastomer such as plastic, rubber, silicone, vinyl, foam, or any combination thereof. It is contemplated in the present invention that connecting member 18 can be formed in various shapes and geometries. In one embodiment, connecting member 18 provides a groove between upper and lower portions 14, 16. The groove (as shown in FIG. 1) can be structured to form a concave shape (e.g., an inward barrel shape). Alternatively, the groove can form a convex shape (e.g., an outward barrel shape). Connecting member 18 is structured to be flexible such that it can move in a hinge-like manner (as shown in FIG. 1). Such hinge-like movement allows upper portion 14 to flex or move independently or separately from and relative to lower portion 16. Thus, mask 10 can provide improved contouring to the user's face, and therefore result in an effective fit. The particular connecting member 18 shown in FIG. 2 is not meant to be limiting and it should be understood that the present invention contemplates a variety of different configurations for flexible connecting member 18. Thus, various flexible connecting members may be substituted for connecting member 18.

In the embodiment as shown in FIG. 2, lower portion 16 also defines lower opening 20. Lower opening 20 can function as a gas inlet. In the embodiment shown in FIG. 1, gas inlet (lower opening 20) can be coupled to a coupling device 21, such as a swivel conduit, for carrying gas, such as air, between mask 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure therapy, as noted above. The particular coupling device 21, shown in FIG. 1, is not meant to be limiting and it should be understood that the present invention contemplates a variety of different coupling devices that could be attached, either permanently or selectively, to lower opening 20 to carry gas to or from mask 10. Thus, a variety of coupling devices (e.g., with or without swivels on one or both ends, and with or without an exhalation system formed integral to the device) may be substituted for coupling device 21.

Respiratory interface device 8, and more specifically brace assembly 40, further includes a strap 30, as shown in FIG. 1. Strap 30 may be directly coupled to either mask 10 or brace assembly 40. Strap 30 may be a tension member or an elastic member. Strap 30 may include an adjustment device, such as, but not limited to, a buckle or a hook-and-loop coupling (neither shown). Such an adjustment device is structured to adjust the relative length of strap 30. Strap 30 is sized to extend about the user's head.

Mask 10 is an oral/nasal mask structured to accommodate both the oral and nasal regions of the user's face. Upper portion 14 can accommodate the nasal region, and lower portion 16 can accommodate the oral region. Mask 10 also includes a patient contacting cushion 15. It is to be understood that mask 10 can a nasal only mask, a nasal cannula, nasal pillows mask, or any other mask that contacts the face of the user. In an exemplary embodiment, cushion 15 is integrally connected to upper portion 14, lower portion 16, and connecting member 18. Cushion 15 is structured to extend toward the user's face and generally defines the depth of mask 10. In an exemplary embodiment, a portion of cushion 15 defines all or at least a portion of connecting member 18. Cushion 15 can be constructed of a wide variety of materials known in the art and can include, but is not limited to, those materials previously described as suitable materials for upper and lower portions 14, 16 and connecting member 18.

The particular cushion 15 shown in FIG. 1 is not meant to be limiting and it should be understood that other types of cushion supports or sealing systems that extend between the frame member (e.g., a faceplate 12 shown in FIG. 1) and the user's face, may be substituted for cushion 15. For example, and without limitation, various cushion configurations can include a double flap cushion, a gel cushion, a gel cushion with a flap, an air-filled cushion, a cushion with a pleat, or multiple cushions (e.g., one inside of the other). Further, it is to be understood that cushion 15 can be detachable and removable from faceplate 12.

Brace assembly 40 includes a brace body 42 and a lever assembly 44. Brace body 42 is a generally rigid body which may be made from a rigid polymer, such as, but not limited to, polycarbonate, nylon, or polyethylene. Brace body 42 includes a central portion 46 and may have one or more extensions 48, discussed below. Brace body central portion 46 has an inner side 50 and an outer side 52. Further, brace body 42 may include a depending sidewall 54 that extends about a portion of brace body central portion 46. Brace body depending sidewall 54 is structured to substantially enclose mask 10. Brace body central portion 46 conforms to the shape of mask 10. For example, in the exemplary embodiment shown, mask 10 is structured to cover the user's nose and mouth, and, mask 10 is, generally, convex when viewed from the outside. Thus, brace body central portion 46, in the exemplary embodiment, is also generally convex. Brace body 42 is coupled to faceplate 12.

In an exemplary embodiment, brace body 42 may further include a spacer device 56 structured to provide a space between mask 10 and brace body 42. As shown, spacer device 56 is a silicone flexure 58. Silicone flexure 58 allows mask 10 to move relative to brace body 42. It is noted that other types of spacer devices 56 may be used. For example, brace body inner side 50 may include an inwardly extending ridge (not shown), or similar construct, structured to provide a space between brace body 42 and mask 10 at locations other than the ridge. Spacer device 56 also provides sufficient space for lever arm body 76, described below, to move between the first and second positions, as described below.

Brace body extension 48, in an exemplary embodiment, is made from the same material as brace body 42 and is unitary therewith. Alternatively, brace body extension 48 may be a separate element (not shown) that is attached to brace body 42. Brace body extension 48 extends outwardly from the central portion 46 and along a facial contour. That is, as used herein, "along a facial contour" means generally parallel to a user's facial contour or following the user's facial contour. Thus, as shown in FIG. 1, one brace body extension 48 is structured to extend over a user's dorsum, over the bridge of the nose, to a location adjacent the user's forehead. Alternatively, one brace body extension 48 may extend from the lower side of brace body 42 and curve under the user's chin (not shown). Brace body extension 48 has a distal end 59. Brace body extension 48 may define a passage 60. Passage 60 is structured to accommodate an actuator coupling member 98, discussed below. That is, passage 60 is sized to allow actuator coupling member 98 to extend through passage 60 and to move therein. Passage 60 may be a closed conduit or an open, or substantially open, channel.

Lever assembly 44 has at least one lever arm 70 and one lever actuator assembly 72 for each lever arm 70. Lever arm 70 has a body 76 with a first end 78 and a second end 80 and a medial portion 82 therebetween. Lever arm body 76 may have any shape, e.g. a circular disk (not shown), but in an exemplary embodiment is elongated. That is, in an exemplary embodiment, lever arm body first end 78 and medial portion 82 are generally elongated and have a longitudinal axis 84.

In one exemplary embodiment, shown in FIG. 1, lever arm body second end 80 is also elongated and disposed along longitudinal axis 84. That is, lever arm body 76 may be a generally straight rod. In another exemplary embodiment, shown in FIG. 3, lever arm body second end 80 is wider than lever arm body first end 78. For example, lever arm body second end 80 may be elongated and perpendicular to longitudinal axis 84. That is, lever arm body 76 may be a generally T-shaped member. In this configuration, lever arm body second end 80 is structured to engage an elongated area on mask 10.

Figure 4:
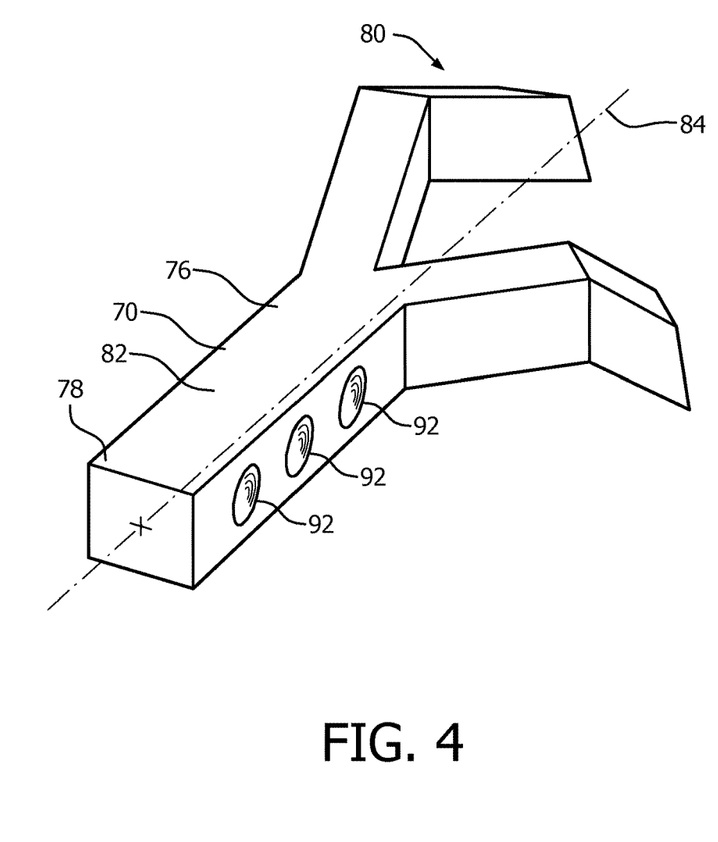
FIG. 4 is a detail isometric view of another embodiment of a lever arm body.

In another exemplary embodiment, shown in FIG. 4, lever arm body second end 80 is Y-shaped. In this configuration, lever arm body second end 80 may engage mask 10 at a location on either side of the user's nose. Further, lever arm body second end 80 may be curled, disposed at an angle to longitudinal axis 84, or otherwise shaped to engage mask 10 in a particular manner For example, a lever arm body second end 80 structured to be disposed at the side of the user's nose, i.e. at the interface of the nose and the cheek, may be shaped as a convex or outwardly extending arcuate surface. Alternatively, a lever arm body second end 80 structured to be disposed over the bridge of the nose may be a concave or inwardly extending arcuate surface. Thus, lever arm body second end 80 may be structured to engage different portions of mask 10 with selectable pressure or bias.

Lever arm body 76 further includes a pivot assembly 90. Pivot assembly 90 is disposed on lever arm body medial portion 82. As used herein, a "pivot assembly" is any construct that allows for a pivotal motion of one element relative to another. As is known, a common pivot construct includes two elements, a passage through the pivoting element and a rod extending therethrough. The rod is coupled to another element and the pivoting element may pivot about the rod. Alternatively, the components may be reversed; that is, the pivoting element may have opposing rods extending therefrom and the other component may have opposed openings therein into which the rods are disposed. Alternatively, the pivot passage described above may be replaced with detents and the rod replaced with hemispheres sized to fit into the detents. In the figures, pivot assembly 90 is represented by an axis of rotation. It is understood that pivot assembly 90 may be, but is not limited to, any of the embodiments identified above. Further, in an exemplary embodiment, lever arm body longitudinal axis 84 is substantially perpendicular to the axis of rotation of pivot assembly 90.

Figure 3:
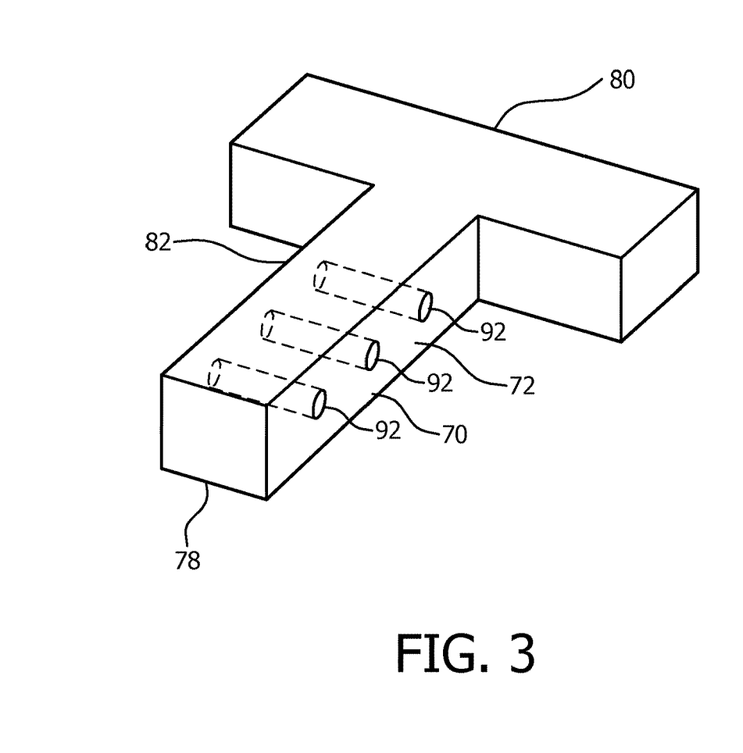
FIG. 3 is a detail isometric view of a lever arm body.

Further, pivot assembly 90 may include a plurality of selectable pivot points 92, as shown in FIGS. 3 and 4. That is, in operation, lever arm body 76 has only one pivot point, but this pivot point may be selected prior to use. In an exemplary embodiment, brace body 42 includes two opposed hemispheres extending toward each other and lever arm body 76 includes a plurality of opposed pairs of detents disposed on opposite sides of an elongated lever arm body medial portion 82. Thus, the user may alter the length of the effective lever arm and the strength of the bias applied to mask 10.

Thus, lever arm body 76 is pivotally coupled to brace body 42 at pivot assembly 90. For example, in an exemplary embodiment, pivot assembly 90 may include a passage (not shown) through lever arm body 76 and a rod (not shown). Pivot assembly rod may be coupled to brace body 42 and extend through pivot passage. In this configuration, lever arm body 76 may pivot about pivot assembly rod. Each lever arm 70 is disposed adjacent to mask 10 and, in an exemplary embodiment, is disposed adjacent to the periphery of mask 10. That is, in an exemplary embodiment, each lever arm 70 is structured to engage mask 10 at, or near, the periphery of mask 10. Thus, lever arm body 76 is disposed adjacent to the periphery of mask 10. Further, in an exemplary embodiment, lever arm body longitudinal axis 84 is generally perpendicular to the adjacent periphery of mask 10. Thus, pivot assembly 90 provides an axis of rotation that is generally parallel to mask 10 periphery adjacent to pivot assembly 90.

As is known, certain areas about the periphery of mask 10 are prone to having less effective sealing surfaces. Thus, at least one lever arm 70 may be disposed at locations selected from: the bridge of the nose, either side of the nose, adjacent a cheek bone, a corner of the mouth, or under the chin.

In this configuration, lever arm body 76 is structured to move between two positions, a first position, wherein lever arm body 76 does not effectively engage a portion of mask 10, and a second position, wherein lever arm body 76 effectively engages a portion of mask 10. Lever arm body 76 may contact either faceplate 12 or cushion 15.

Figure 5:
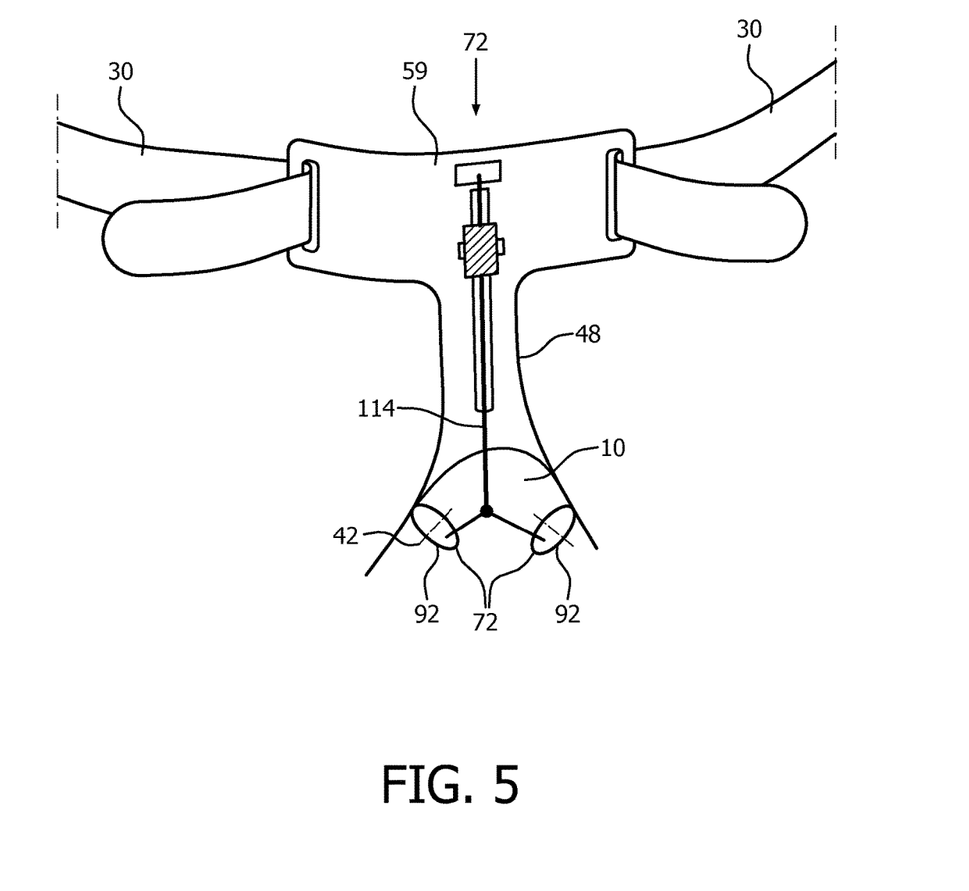
FIG. 5 is a front view of a respiratory interface device according to another embodiment of the invention.

Each lever actuator assembly 72 includes a lever arm body actuator coupling 96, an actuator coupling member 98, and an associated actuator member 94. As used herein, actuator member 94 is "associated" with a lever arm body 76 when actuator member 94 causes lever arm body 76 to move between its first and second positions. That is, in one exemplary embodiment, shown in FIG. 1, there will be lever arm body actuator coupling 96 and actuator coupling member 98 per lever arm body 76, but, as shown in FIG. 5, in another exemplary embodiment, one actuator member 94 may actuate more than one lever arm body. Thus, there may be more lever arm bodies 76 than actuator members 94 within lever assembly 44.

Lever arm body actuator coupling 96 is disposed on lever arm body first end 78. Lever arm body actuator coupling 96 is structured to be coupled to actuator coupling member 98. In an exemplary embodiment, shown in FIG. 1, there is a single lever arm body actuator coupling 96 on lever arm body 76. In another exemplary embodiment, shown in FIG. 6, there are two lever arm body actuator couplings 96 on lever arm body 76. As lever arm body actuator coupling 96 is disposed on lever arm body first end 78, lever body second end 80 is structured to engage mask 10.

Actuator coupling member 98 has a first end 100 and a second end 102. Actuator coupling member first end 100 is coupled to actuator member 94 and actuator coupling member second end 102 coupled to Lever arm body actuator coupling 96. Actuator member 94 is movably coupled to brace body 42 and is structured to move between a first position and a second position.

The motion of actuator member 94 is transferred, via actuator coupling member 98, to lever arm body 76. Thus, when actuator member 94 is in the first position, any associated lever arm body 76 is in the first position, and, when actuator member 94 is in the second position, any associated lever arm body 76 is in the second position. Specific embodiments of various actuator assemblies 72 are discussed below. It is noted that actuator assemblies 72, generally are structured to move any associated lever arm body 76 is one direction, typically from the first position to the second position. In an exemplary embodiment, movement of a lever arm body 76 from the second position to the first position is caused by the resiliency of mask 10. That is, when the bias created by the effective engagement of lever arm body 76 to mask 10 is removed, mask 10 will return to an undeformed configuration. In returning to an undeformed configuration, mask 10 causes lever arm body 76 to move from the second position to the first position.

Thus, while movement of actuator coupling member 98 does not directly cause lever arm body 76 to move from the second position to the first position, it is still accurate to state that motion of actuator member 94 between the first and second position is transferred via actuator coupling member 98 to lever arm body 76 causing, directly or indirectly, lever arm body 76 to move between lever arm body 76 first and second positions. That is, the position of actuator member 94 corresponds to the position of an associated lever arm body 76. Further, before discussing specific embodiments of various actuator assemblies 72, it is noted that, so long as lever assembly 44 includes "at least one" one lever arm 70, it is accurate to state that lever assembly 44 also includes "at least one" lever actuator assembly 72 or "at least one" of a specific embodiment of an actuator assembly 72 and its various component.

Figure 6:
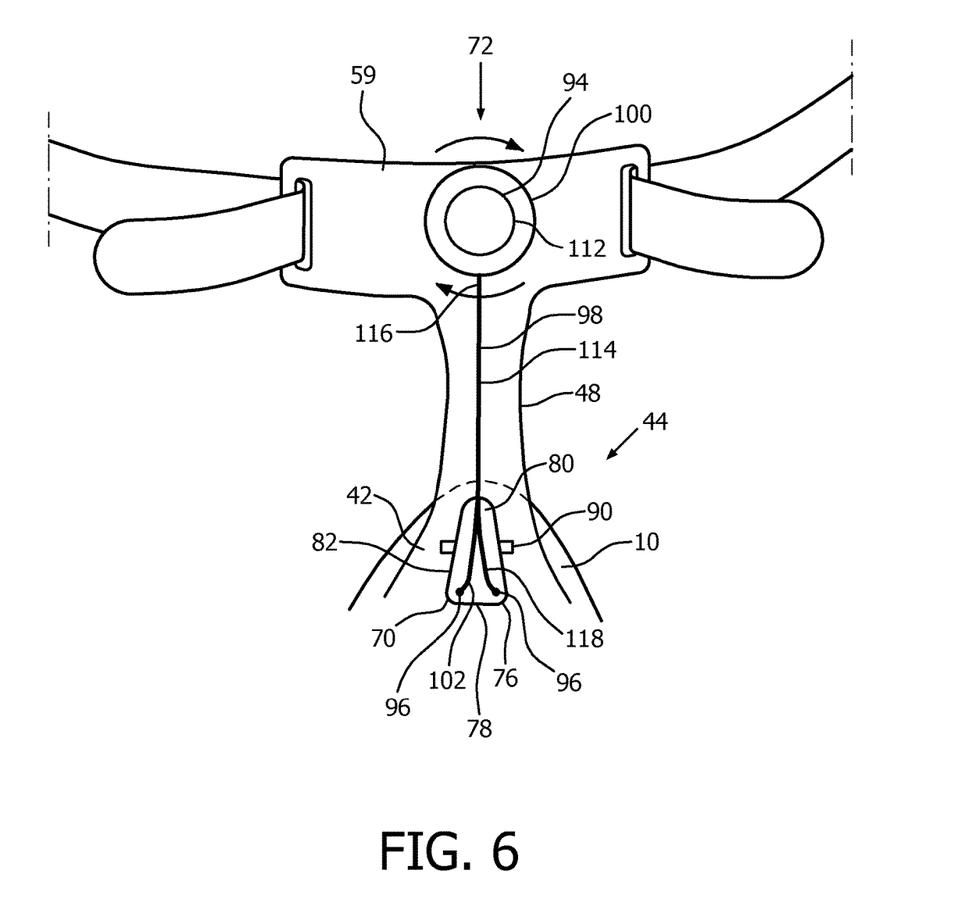
FIG. 6 is a front view of a respiratory interface device according to another embodiment of the invention.

Thus, as shown in FIG. 6, in one exemplary embodiment, at least one actuator member 94 is a knob 110 having an axially extending spool 112. Further, at least one actuator coupling member 98 is a tension member 114 having a first end 116 and a second end 118. Tension member first end 116 is structured to wind about, and unwind from, spool 112. Tension member second end 118 is coupled to lever arm body actuator coupling 96. Thus, as a user, utilizing knob 110, winds tension member 114 about spool 112, i.e. moves actuator member 94 from a first position to a second position, the unspooled length of tension member 114 is reduced and lever arm body 76 moves from the first position to the second position. When the user unwinds tension member 114 about spool 112, i.e. moves actuator member 94 from a second position to a first position, the unspooled length of tension member 114 increases and lever arm body 76, assisted by the resiliency of mask 10, moves from the second position to the first position.

In another exemplary embodiment, shown in FIG. 2, at least one actuator member 94 is a knob 120 having an axially extending threaded rod 122. Actuator member threaded rod 122 is disposed in a threaded opening 124 in brace body 42. Actuator member threaded rod 122 is actuator coupling member 98. Actuator member threaded rod 122 has a distal end 126. Actuator member threaded rod distal end 126 is coupled to lever arm body actuator coupling 96. That is, lever arm body actuator coupling 96 may be just the surface of lever arm body 76 but, in an exemplary embodiment, lever arm body actuator coupling 96 is a wear resistant platform 128. Actuator member threaded rod distal end 126 engages lever arm body actuator coupling 96 when actuator member 94, i.e. knob 120, is moved to the first position. It is noted that in this embodiment, lever arm body actuator coupling 96 is disposed at lever arm body second end 80 as opposed to lever arm body first end 78. Thus, a user may rotate knob 120 between a first and second position. As knob 120 rotates, actuator member threaded rod 122 moves in and out of threaded opening 124 and actuator member threaded rod distal end 126 moves toward or away from wear resistant platform 128. Engagement of actuator member threaded rod distal end 126 with wear resistant platform 128 causes lever arm body 76 to move between its first and second positions.

Figure 7:
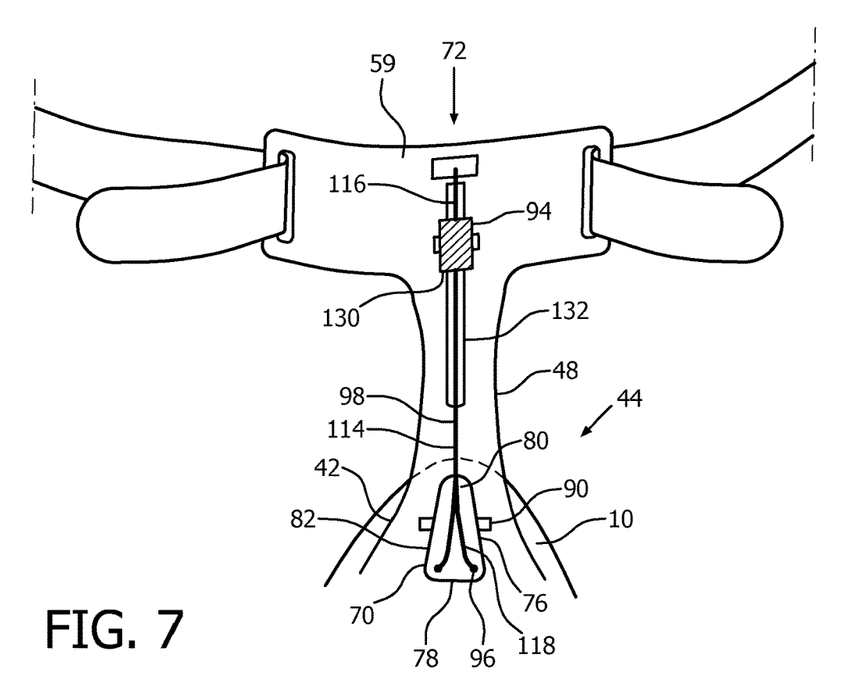
FIG. 7 is a front view of a respiratory interface device according to another embodiment of the invention.
Figure 8:
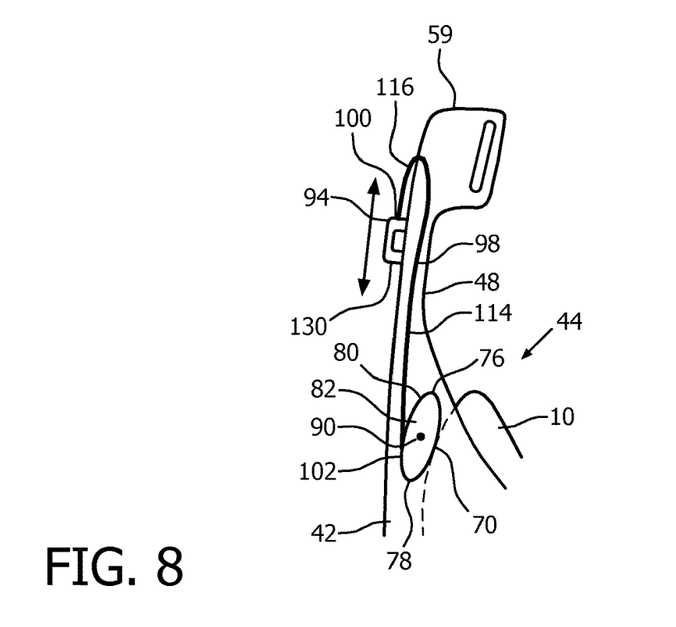
FIG. 8 is a side view of a respiratory interface device shown in FIG. 7.

In another exemplary embodiment, shown in FIGS. 7 and 8, at least one actuator member 94 is a slider 130 structured to move over brace body outer side 52. Slider 130 may be disposed in a race 132, or, in an exemplary embodiment, slider 130 includes an extension (not shown) extending into race 132. Race 132 may be structured to snugly engage slider 130 or its extension. Thus, slider 130 will not move in race 132 without action by the user. As in the first embodiment described above, actuator coupling member 98 is a tension member 114 having a first end 116 and a second end 118. In this embodiment, tension member first end 114 is coupled to slider 130 and tension member second end 118 is coupled to Lever arm body actuator coupling 96. In this embodiment, a user slides slider 130 between a first and second position causing tension member 114 to move. As tension member 114 moves, lever arm body 76 moves between its first and second positions. It is noted that, as shown in FIG. 8, tension member 114 may extend over a path that doubles back on itself, e.g. extending upwardly along brace body central portion inner side 50 and downwardly over brace body central portion outer side 52.

Figure 9:
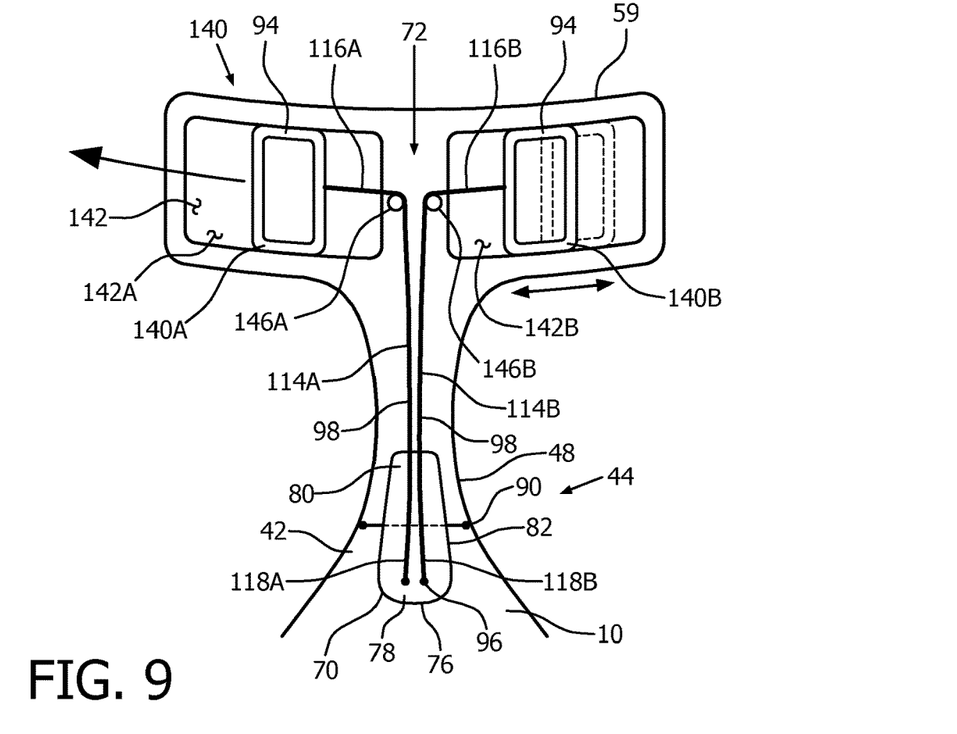
FIG. 9 is a back view of a respiratory interface device according to another embodiment of the invention.

In another exemplary embodiment, shown in FIG. 9, at least one actuator member 94 is at least one strap buckle slider 140. Strap buckle slider 140 is structured to be coupled to strap 30. Brace body 42 includes at least one strap buckle slider socket 142 structured to have strap buckle slider 140 movably disposed therein. As shown in an exemplary embodiment, there are two strap buckle slider sockets 142A, 142B disposed at brace body extension distal end 58. A strap buckle slider socket 142 may, however, be disposed at any location on mask 10. Each strap buckle slider 140A, 140B is movably disposed in an associated strap buckle slider socket 142A, 142B. Each strap buckle slider 140A, 140B is structured to translate within associated strap buckle slider socket 142A, 142B. That is, as used herein, "translate" means to move without rotation or angular displacement. In an exemplary embodiment, actuator member 94 first position, i.e. strap buckle slider 140A, 140B first position, is closer to the centerline of the user's face, and, actuator member 94 second position, i.e. strap buckle slider 140A, 140B second position is located laterally outwardly therefrom.

In this configuration, strap 30 may be coupled to both strap buckle slider 140A, 140B and will extend laterally relative to the user's face. That is, a portion of strap 30 loops through each strap buckle slider 140A, 140B leaving the distal ends of strap 30 exposed. Further, in this configuration, a user may grip the distal ends of strap 30 and may tighten strap 30 about the user's head by pulling on strap 30 distal ends. The motion of strap 30 causes each strap buckle slider 140A, 140B to move from the first position to the second position.

In this exemplary embodiment, actuator coupling member 98 is at least one, and as shown two, tension members 114A, 114B each having a first end 116A, 116B and a second end 118A, 118B, respectively. Each tension member first end 116A, 116B is coupled to an associated strap buckle slider 140A, 140B. Each tension member second end 118A, 118B is coupled to Lever arm body actuator coupling 96. As noted above, actuator members 94, i.e. strap buckle sliders 140A, 140B, move laterally. Thus, brace body 42 includes posts 146A, 146B over which tension members 114A, 114B pass and turn about 90 degrees. In an exemplary embodiment, posts 146A, 146B have rounded exterior surfaces. Thus, as strap buckle sliders 140A, 140B move between their first and second positions, lever arm body 76 moves between its first and second positions.

Figure 10:
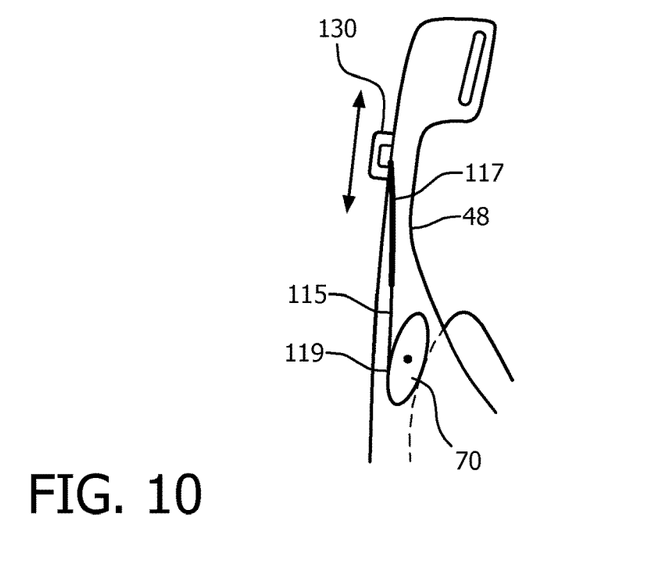
FIG. 10 is a side view of a respiratory interface device according to another embodiment of the invention.

It is noted that rather than posts 146A, 146B, tension members 114A, 114B may extend through a passage 60 defining a right angle (not shown). Moreover, in any of the embodiments above that utilize a tension member 114, tension member may extend through passage 60. Further, any of the embodiments above that utilize tension member 114 may also use a semi-flexible member 115, as shown in FIG. 10 instead of tension member 114.

Other than the nature of the material used to make semi-flexible member 115, semi-flexible member 115 is otherwise similar to tension member 114. That is, semi-flexible member 115 has a first end 117 and a second end 119 that are coupled to other elements in a manner similar to tension member 114 as described above. Accordingly, for example, semi-flexible member 115 may extend between and be coupled to, slider 130 and Lever arm body actuator coupling 96 in a manner substantially similar to the embodiment described above. If semi-flexible member 115 is used, a semi-flexible member second end 119 may be rotatably coupled to Lever arm body actuator coupling 96. As semi-flexible member 115 is more rigid than tension member 114, movement of actuator member 94 from the second position to the first position causes lever arm body 76 to move between its second and first positions. That is, the resiliency of mask 10 would not be the only force action on lever arm body 76 to move it between its second and first positions.

Figure 11:
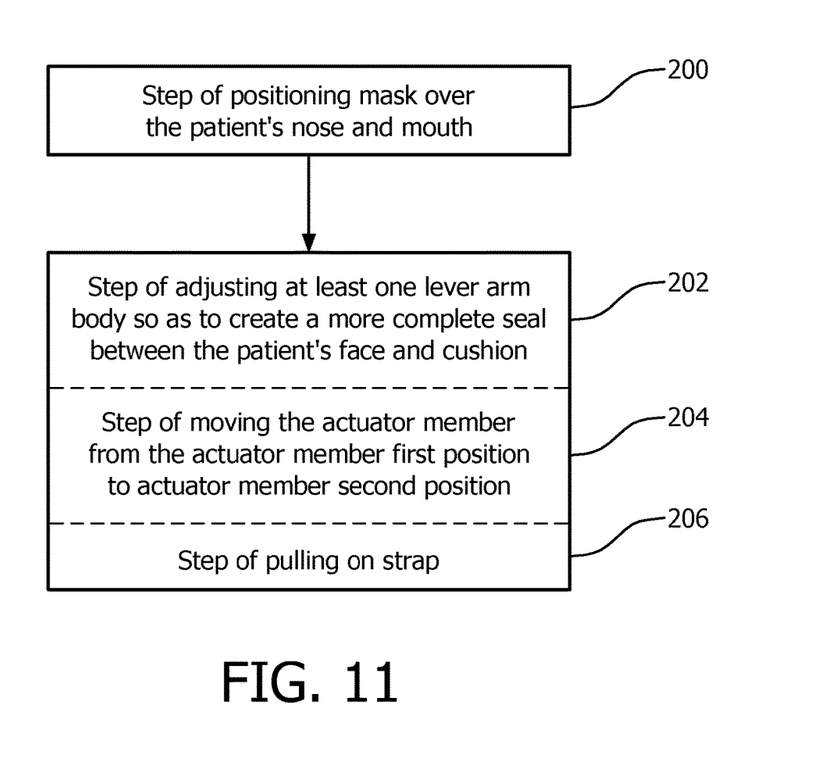
FIG. 11 is a flow chart of the method steps associated with using the respiratory interface device.

As shown in FIG. 11, a method of utilizing respiratory interface device 8 includes the steps of positioning 200 mask 10 over the patient's nose and mouth thereby creating a generally continuous seal between the patient's face and patient contacting cushion 15. Then, adjusting 202 at least one lever arm body 76 so as to create a more complete seal between the patient's face and cushion 15. Further, the step of adjusting the at least one adjustable coupling so as to create a more complete seal between the patient's face and cushion 15 includes the step of moving 204 the actuator member 94 from actuator member 94 first position to actuator member 94 second position. Further, as noted above, in one exemplary embodiment at least one actuator member 94 is at least one strap buckle slider 140. Strap buckle slider 140 is coupled to strap 30 having an exposed distal end. When a user pulls on strap 30 distal end, strap buckle slider 140 moves from the first position to the second position. Accordingly, the step of moving the actuator member from the first position to the second position may include the step of pulling 206 on strap 30.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by on and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
   a mask having a faceplate and a patient contacting cushion, wherein the patient contacting cushion is coupled to and extends about the faceplate,
   a brace assembly having a brace body and a lever assembly, wherein the brace body has a central portion having an outer side and an inner side, wherein the central portion is structured to be coupled to the mask faceplate,
   wherein the brace body is coupled to the faceplate,
   wherein the lever assembly includes at least one lever arm and one actuator assembly,
   wherein the at least one lever arm includes a body with a first end and a second end and a medial portion therebetween, wherein the lever arm body further includes a pivot assembly disposed on the lever arm body medial portion, wherein the lever arm body is pivotally coupled to the brace body at the pivot assembly,
   wherein each lever arm body is structured to move between two positions, a first position, wherein the lever arm body does not effectively engage a portion of the mask, and a second position, wherein the lever arm body effectively engages a portion of the mask,
   wherein the lever arm body is disposed adjacent to the periphery of the mask, and wherein the lever arm body pivot assembly provides an axis of rotation that is generally parallel to the adjacent mask periphery, and
   wherein for each lever arm body, the lever actuator assembly includes a lever arm body actuator coupling, an actuator coupling member, and an associated actuator member, wherein the lever arm body actuator coupling is disposed on one of the lever arm body first end or lever arm body second end, wherein the lever body second end is structured to engage the mask, wherein the actuator member is movably coupled to the brace body and structured to move between a first position and a second position, wherein the actuator coupling member has a first end and a second end, wherein the actuator coupling member first end is coupled to the actuator member and the actuator coupling member second end is coupled to the lever arm body actuator coupling, and wherein motion of the actuator member between the first and second position is transferred via the actuator coupling member to the lever arm body causing the lever body to move between the lever arm body first and second positions.

2. The respiratory interface device of claim 1, wherein the at least one actuator member is a knob having an axially extending spool, wherein the at least one actuator coupling member is a tension member having a first end and a second end, wherein the tension member first end is structured to wind about, and unwind from, the spool, and wherein the tension member second end being coupled to the lever arm body actuator coupling.

3. The respiratory interface device of claim 1, wherein at least one actuator member is a knob having an axially extending threaded rod, the threaded rod being the actuator coupling member, wherein the brace body has at least one threaded opening corresponding to the actuator member threaded rod, wherein the actuator member threaded rod having a distal end; and wherein the actuator member threaded rod having a distal end is coupled to the lever arm body actuator coupling.

4. The respiratory interface device of claim 1, wherein at least one actuator member is a slider structured to move over the brace body outer side, wherein the at least one actuator coupling member is a tension member having a first end and a second end, wherein the tension member first end is coupled to the slider, and wherein the tension member second end is coupled to the lever arm body actuator coupling.

5. The respiratory interface device of claim 1, wherein at least one actuator member is a slider structured to move over the brace body outer side, wherein the at least one actuator coupling member is a semi-flexible member having a first end and a second end, wherein the semi-flexible member first end is coupled to the slider; and, wherein the semi-flexible member second end is coupled to the lever arm body actuator coupling.

6. The respiratory interface device of claim 1, wherein the brace assembly includes at least one strap and a strap buckle slider socket, wherein at least one actuator member is a strap buckle slider, wherein the strap buckle slider is structured to be coupled to the strap and is structured to move within the strap buckle slider socket, wherein the at least one actuator coupling member is a tension member having a first end and a second end, wherein the tension member first end is coupled to the strap buckle slider, and wherein the tension member second end is coupled to the lever arm body actuator coupling.

7. The respiratory interface device of claim 1, wherein the brace body has at least one extension, the at least one extension extending outwardly from the central portion and along a facial contour and having a distal end; and wherein the at least one actuator coupling member is disposed at the at least one extension distal end.

8. The respiratory interface device of claim 7, wherein the brace body at least one extension defines a passage, the passage extending between a first location adjacent the actuator member, when the actuator member is in the first position, and a second location adjacent the lever body; and wherein the actuator coupling member is movably disposed in the passage.

9. The respiratory interface device of claim 7, wherein the brace assembly includes at least one strap and a strap buckle slider socket, wherein the at least one actuator member is a strap buckle slider, the strap buckle slider structured to be coupled to the strap and structured to move within the strap buckle slider socket, wherein the at least one actuator coupling member is a tension member having a first end and a second end, wherein the tension member first end is coupled to the strap buckle slider; and wherein the tension member second end is coupled to the lever arm body actuator coupling.

10. A respiratory interface device comprising:
a mask having a faceplate and a patient contacting cushion, wherein the patient contacting cushion is coupled to and extends about the faceplate;
a brace assembly having a brace body and a lever assembly, wherein the brace body has a central portion having an outer side and an inner side, wherein the central portion is structured to be coupled to the mask faceplate;
wherein the brace body is coupled to the faceplate, wherein the lever assembly includes at least one lever arm and one actuator assembly,
wherein the at least one lever arm includes a body with a first end and a second end and a medial portion therebetween, wherein the lever arm body further includes a pivot assembly disposed on the lever arm body medial portion, wherein the lever arm body is pivotally coupled to the brace body at the pivot assembly,
wherein each lever arm body is structured to move between two positions, a first position, wherein the lever arm body does not effectively engage a portion of the mask, and a second position, wherein the lever arm body effectively engages a portion of the mask;
wherein the lever arm body first end and medial portion are generally elongated and have a longitudinal axis, and wherein the lever arm body second end is wider than the lever arm body first; and
wherein the lever arm body second end is Y-shaped.

11. A method of using a respiratory interface device, the respiratory interface device including a mask having a faceplate and a patient contacting cushion, the patient contacting cushion coupled to, and extending about, the faceplate, a brace assembly having a brace body and a lever assembly, the brace body having a central portion, the central portion having an outer side and an inner side, the central portion being structured to be coupled to the mask faceplate, the brace body being coupled to the mask faceplate, the lever assembly having at least one lever arm and one lever actuator assembly for each lever arm, the lever arm having a body with a first end and a second end with a medial portion therebetween, the lever arm body further including a pivot assembly disposed on the lever arm body medial portion, the lever arm body being pivotally coupled to the brace body at the pivot assembly, and the lever arm body structured to move between two positions, a first position, wherein the lever arm body does not effectively engage the mask, and a second position, wherein the lever arm body effectively engages the mask, wherein the at least one actuator assembly includes an actuator member associated with the at least one lever arm body, the actuator member structured to move between a first position and a second position, wherein for each lever arm body, the lever actuator assembly includes, a lever arm body coupling, an actuator coupling member, and an associated actuator member, the lever arm body actuator coupling disposed on the lever arm body first end, the lever body second end structured to engage the mask; and the actuator member movably coupled to the brace body and structured to move between the first position and the second position, the actuator coupling member having a first end and a second end, the actuator coupling member first end coupled to the actuator member and the actuator coupling member second end coupled to the lever arm body actuator coupling, wherein motion of the actuator member between the first and second position is transferred via the actuator coupling member to the lever arm body causing the lever body to move between the lever arm body first and second positions, and wherein the brace assembly includes at least one strap and a strap buckle slider socket, the at least one actuator member is a strap buckle slider, the strap buckle slider structured to be coupled to the strap and structured to move within the strap buckle slider socket, the at least one actuator coupling member is a tension member having a first end and a second end, wherein the tension member first end is coupled to the strap buckle slider; the tension member second end is coupled to the lever arm body actuator coupling, and the strap being coupled to the strap buckle slider with a distal end of the strap being exposed, the method comprising:

positioning the mask over the patient's nose and mouth thereby creating a generally continuous seal between the patient's face and the cushion, adjusting at least one lever arm body so as to create a more complete seal between the patient's face and the cushion, wherein the step of adjusting the at least one adjustable coupling so as to create a more complete seal between the patient's face and the patient contacting cushion includes the step of: moving the actuator member from the first position to the second position, and wherein the step of moving the actuator member from the first position to the second position includes the step of: pulling on the strap.

\* \* \* \* \*